(12) United States Patent
Benyamini et al.

(10) Patent No.: US 8,079,710 B2
(45) Date of Patent: Dec. 20, 2011

(54) DUAL POSITION OPHTHALMIC APPARATUS

(75) Inventors: Gideon Hanoch Benyamini, Ramat Hasharon (IL); Alon Goldenberg, Rehovot (IL); Omer Rafaely, Tel Aviv (IL); Yair Mandelstam-Manor, Tel Aviv (IL); Elisha Avraham Tal, Nataf (IL); Eitan Sharif, Kibbutz Gesher-Haziv (IL)

(73) Assignee: Notal Vision Ltd., Tel Aviv (IL)

( * ) Notice: Subject to any disclaimer, the term of this patent is extended or adjusted under 35 U.S.C. 154(b) by 541 days.

(21) Appl. No.: 11/972,009

(22) Filed: Jan. 10, 2008

(65) Prior Publication Data

US 2009/0180074 A1  Jul. 16, 2009

(51) Int. Cl.
  *A61B 3/02* (2006.01)
(52) U.S. Cl. ............ 351/223; 351/237; 351/239
(58) Field of Classification Search ............ 351/200, 351/222–226, 239–246, 205, 206, 208, 211, 351/237; 606/4
  See application file for complete search history.

(56) References Cited

U.S. PATENT DOCUMENTS

| | | | |
|---|---|---|---|
| 3,082,763 A | 3/1963 | McLaughlin, Jr. | |
| 4,452,515 A | 6/1984 | Lewis | |
| 4,740,072 A | 4/1988 | Griffin et al. | |
| 4,756,305 A | 7/1988 | Mateik et al. | |
| 5,805,270 A * | 9/1998 | Marshall | 351/222 |
| 5,838,424 A | 11/1998 | Wawro et al. | |
| 6,656,131 B2 | 12/2003 | Alster et al. | |
| 6,742,892 B2 | 6/2004 | Liberman | |
| 7,275,830 B2 | 10/2007 | Alster et al. | |
| 2007/0121070 A1 | 5/2007 | Alster et al. | |
| 2007/0159598 A1 * | 7/2007 | Yancey et al. | 351/206 |

* cited by examiner

*Primary Examiner* — Ricky Mack
*Assistant Examiner* — Mahidere Sahle
(74) *Attorney, Agent, or Firm* — Simon Kahn

(57) ABSTRACT

An ophthalmic apparatus exhibiting a first position and a second position related by a rotation of 180° about a longitudinal axis. Automatic detection of the position is preferably provided, and the results of the detection are communicated to a computing unit portion of the ophthalmic apparatus. The ophthalmic apparatus exhibits: a first formation for receiving a user's head in the first position, which is in one embodiment a generally curved formation approximating the shape of the user's lower forehead preferably with an indent portion for receiving the user's nose when the ophthalmic apparatus in the second position; and a second formation for receiving a user's head in the second position, which is in one embodiment a generally curved formation approximating the shape of the user's lower forehead preferably with an indent portion for receiving the user's nose when the ophthalmic apparatus in the first position.

18 Claims, 5 Drawing Sheets

DUAL POSITION OPHTHALMIC APPARATUS

BACKGROUND OF THE INVENTION

The invention relates generally to the field of ophthalmic apparatuses and more particularly to a two position ophthalmic apparatus wherein the positions are determined by rotation about a longitudinal axis.

Eye testing is performed on a regular basis for patients of various ages to evaluate vision and to check for the presence of eye diseases such as, without limitation, cataracts, glaucoma, macular degeneration and diabetic retinopathy. One test often performed is a visual field test which evaluates whether the patient has difficulty seeing in any areas of their peripheral vision.

Perimetry is the systematic measurement of differential light sensitivity in the visual field by the detection of the presence of test targets on a defined background. Perimetry can be clinically performed with confrontational field testing, in which the patient's gaze is held fixed on a target, while objects are presented at various places in the visual field. Inputs received by the patient responsive to the presented objects are used to automatically map and quantify the visual field testing.

Static perimetry involves the presentation of repeated stimuli at increasing levels of intensity until the stimulus is detected by the patient. Kinetic perimetry involves the presentation of a moving stimulus of a particular size and intensity. The stimulus is moved from an area outside of the visual field towards the fixation target until it is detected by the user.

Perimetry typically requires independent testing of each eye, because images perceived by the other eye may affect the results of the tested eye, and a record of the test must be associated with the eye being tested. Thus, the perimetry device must provide a means for selecting the eye to be tested, a means for occluding the non-selected eye, and a means for coordinating the testing and the results with the selection of the eye to be tested. Similarly other eye tests, such as tests for visual acuity and contrast sensitivity, are best accomplished with a means for selecting the eye to be tested, a means for occluding the non-selected eye, and a means for coordinating the testing and the results with the selection of the eye to be tested.

U.S. Pat. No. 6,656,131 issued Dec. 2, 2003 to Alster et al, U.S. Pat. No. 7,275,830 issued Oct. 2, 2007 to Alster et al, and U.S. Patent Application Publication S/N 2007/0121070 A1 published May 31, 2007 to Alster et al, the entire contents of each of which are incorporated herein by reference, are addressed to methods and systems for detecting eye disease. Such perimetry devices are designed for use by qualified personnel and as such result in infrequent use by any particular patient. Generally, the requirement to visit a physician to perform a test results in infrequent testing due to the added cost and inconvenience of arranging such a test with a physician.

Certain diseases of the eye may progress rapidly, and frequent follow up is thus desirable. As indicated above, testing by a physician, or other qualified personnel, results in reduced frequency of testing. It is to be noted that the need for frequent follow up is often a function of the age of the patient. Unfortunately, as patients age their ability to learn, and/or handle, sophisticated equipment, often declines. Thus it would be desirable to provide an eye testing apparatus which can be used by the patient without the intervention of qualified personnel.

Vision therapy devices, including without limitation eye training and eye exercise devices are known in the art. Such vision therapy devices are utilized by a patient, or a user, to improve or stabilize an eye condition, in particular without limitation one of low vision, amblyopia, myopia and strabismus. Such vision therapy devices would be positively impacted by the existence of a dual position ophthalmic apparatus designed for use by a patient without intervention of qualified personnel.

The terms patient and user, as used throughout this document, are used interchangeably and are meant to be directed to the subject having the eye being tested or for whom the vision therapy is directed.

What is needed is a simple low cost eye testing or eye therapy device, generally termed an ophthalmic apparatus, which is operable by a user without requiring qualified trained personnel.

SUMMARY OF THE INVENTION

Accordingly, it is a principal object of the present invention to provide a low cost, home use ophthalmic apparatus. In one embodiment this is accomplished by an ophthalmic apparatus exhibiting two positions. The ophthalmic apparatus is changed from a first position to a second position by rotation of the apparatus 180° about a longitudinal axis of the eye testing apparatus. Automatic detection of the position is preferably provided, and the results of the detection are communicated to a computing equipment portion of the ophthalmic apparatus.

The ophthalmic apparatus exhibits a first formation for receiving a user's head in a first position, which is a generally curved formation approximating the shape of the user's lower forehead. The first formation preferably exhibits an indent portion for receiving the user's nose when the ophthalmic apparatus is in the second position.

The ophthalmic apparatus exhibits a second formation for receiving a user's head in a second position, which is a generally curved formation approximating the shape of the user's lower forehead. The formation preferably exhibits an indent portion for receiving the user's nose when the ophthalmic apparatus is in the first position.

The ophthalmic apparatus further exhibits a single target object arranged to be in optical communication with the user's first eye when the ophthalmic apparatus is in the first position and to be in optical communication with the user's second eye when the ophthalmic apparatus is in the second position. The single target object is preferably in communication with the computing unit portion of the ophthalmic apparatus.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. In the accompanying drawing.

DETAILED DESCRIPTION OF THE PREFERRED EMBODIMENTS

Figure 1:
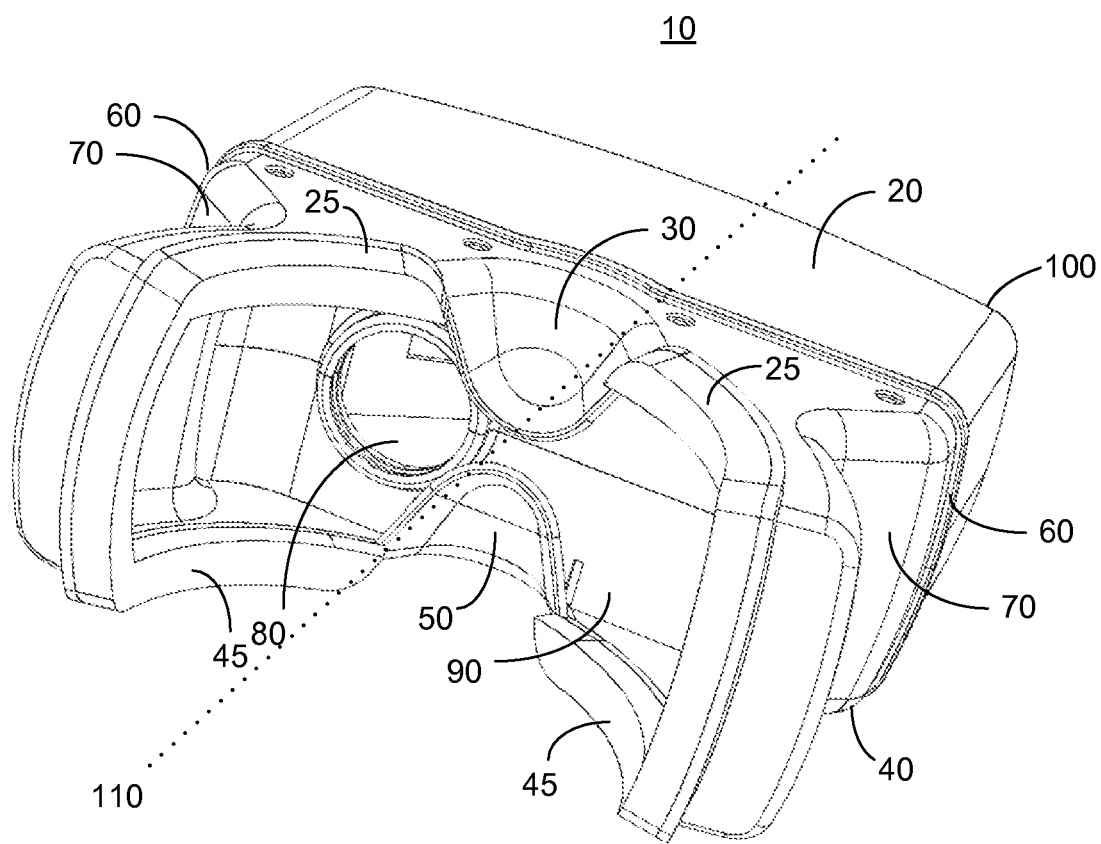
FIG. 1 illustrates a perspective view of an embodiment of an ophthalmic apparatus in accordance with a principle of the current invention in a first position.

The present embodiments enable an eye testing device. In one embodiment this is accomplished by an ophthalmic apparatus exhibiting two positions. The ophthalmic apparatus is changed from a first position to a second position by rotation of the apparatus 180° about a longitudinal axis of the ophthalmic apparatus. Automatic detection of the position is preferably provided, and the results of the detection are communicated to a computing equipment portion of the ophthalmic apparatus.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

FIG. 1 illustrates an embodiment of an ophthalmic apparatus 10 in accordance with a principle of the invention, in a first position, comprising: a top wall 20; a top wall formation 25 exhibiting a first indent portion 30; a bottom wall 40; a bottom wall formation 45 exhibiting a second indent portion 50; a pair of side walls 60 each comprising a side indent 70; an target object 80; an occlusion member 90; and a back wall 100. Ophthalmic apparatus 10 further exhibits a longitudinal axis 110, located between top wall 20 and bottom wall 40. Top wall formation 25 defines an end of top wall 20, and top wall 20 generally extends away from top wall formation 25. Bottom wall formation 45 defines an end of bottom wall 40, and bottom wall 40 generally extends away from bottom wall formation 45. Top wall 20 is generally opposite bottom wall 40. Back wall 100 connects the end of top wall 20 opposite top wall formation 25 to the end of bottom wall 40 opposite bottom wall formation 45. Each side wall 60 connects one side of top wall 20 to a corresponding side of bottom wall 40 thereby forming an enclosure. Side indents 70 are optionally included as part of side walls 60 to aid the user in holding ophthalmic apparatus 10.

In operation, to test, or perform therapy upon, the user's first eye, shown here as the left eye, ophthalmic apparatus 10 is held to the user's face with top wall 20 facing the user's head top and with top wall formation 25 placed again the user's forehead. Preferably top wall 20 exhibits instructions indicating that top wall formation 25 should be placed against the lower forehead. The user's nose is comfortably accommodated by second indent portion 50, thereby obtaining optical communication between the user's first eye and target object 80. Occlusion member 90 occludes the user's second eye. First indent portion 30 and second indent portion 50 cooperate to occlude extraneous light, including ambient light, from the user's first eye. In one embodiment, (not shown) an extension of first indent portion 30 reaches second indent portion 50 thereby further aiding in occluding extraneous light. Longitudinal axis 110 generally meets the bridge of the user's nose and extends in a direction generally orthogonal to a plane defined by the user's face. The term target object as used herein is meant to include an optical object used for any of testing and therapy, without limitation, for the eye within optical communication therewith. In one embodiment the optical object is a screen displaying one or more images.

Figure 2:
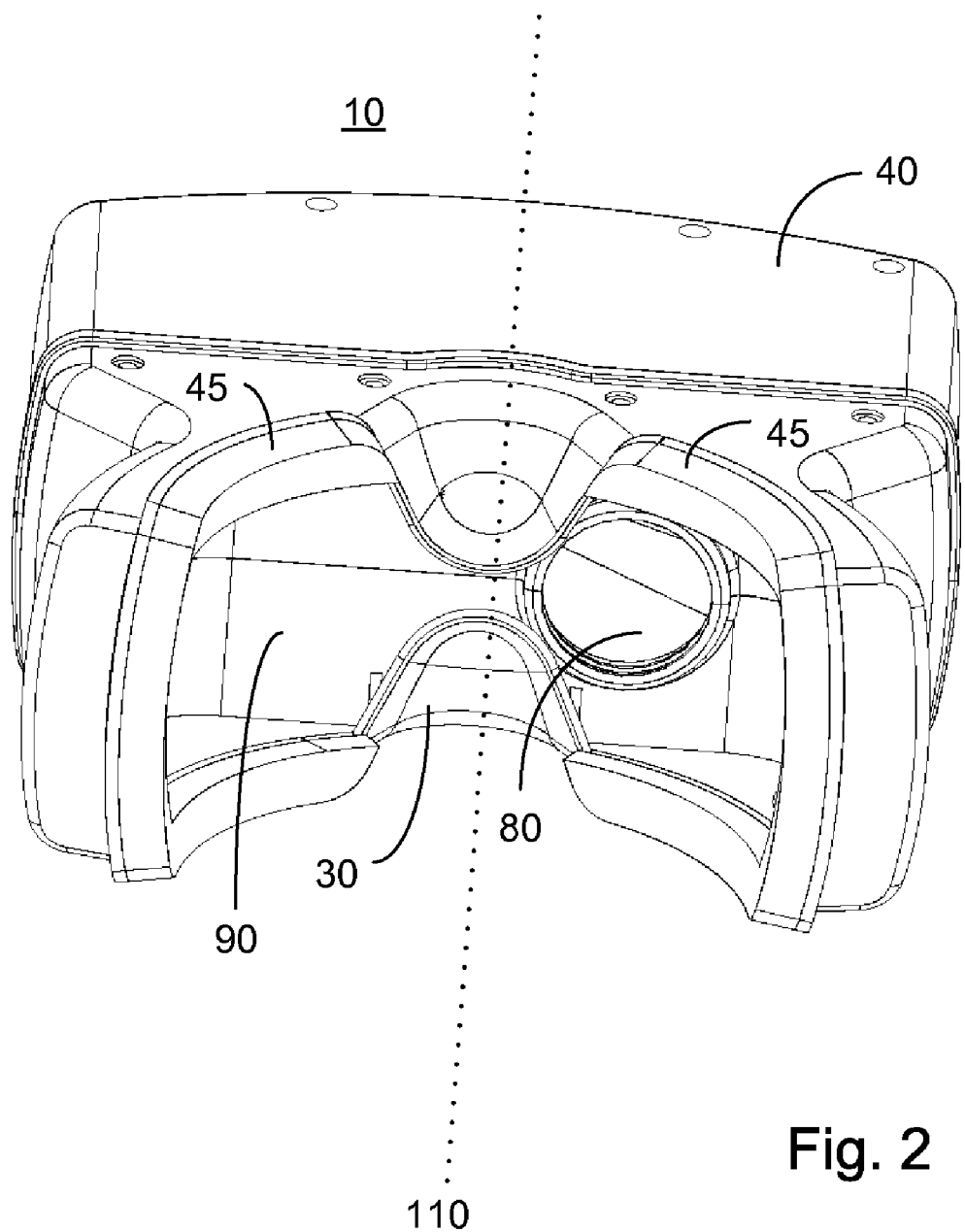
FIG. 2 illustrates a perspective view of an embodiment of an ophthalmic apparatus in accordance with a principle of the current invention in a second position.

To test, or perform therapy upon the user's second eye, ophthalmic apparatus 10 is removed from the user's face and rotated 180° about longitudinal axis 110 to the second position. FIG. 2 illustrates a perspective view of an embodiment of ophthalmic apparatus 10 in accordance with a principle of the current invention in the second position. Ophthalmic apparatus 10 is held to the user's face with bottom wall 40 facing up and with bottom wall formation 45 placed again the user's forehead. Preferably bottom wall 40 exhibits instructions indicating that bottom wall formation 45 should be placed against the lower forehead. The user's nose is comfortably accommodated by first indent portion 30, thereby obtaining optical communication between the user's second eye and target object 80. Occlusion member 90 occludes the user's first eye. Longitudinal axis 110 generally meets the bridge of the user's nose and extends in a direction generally orthogonal to a plane defined by the user's face.

Figure 6:
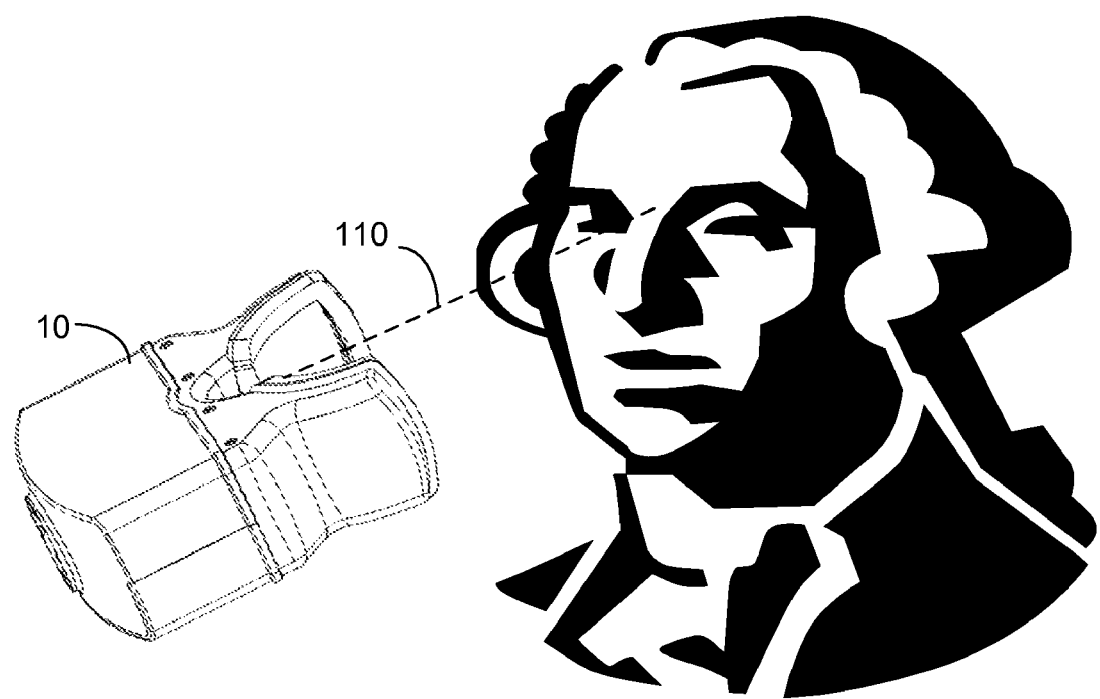
FIG. 6 illustrates the longitudinal axis generally directed toward the bridge of the user's nose.

FIG. 6 illustrates longitudinal axis 110 of ophthalmic apparatus 10 generally directed toward the bridge of the user's nose, and orthogonal to a plane generally defined by the user's face.

Figure 3:
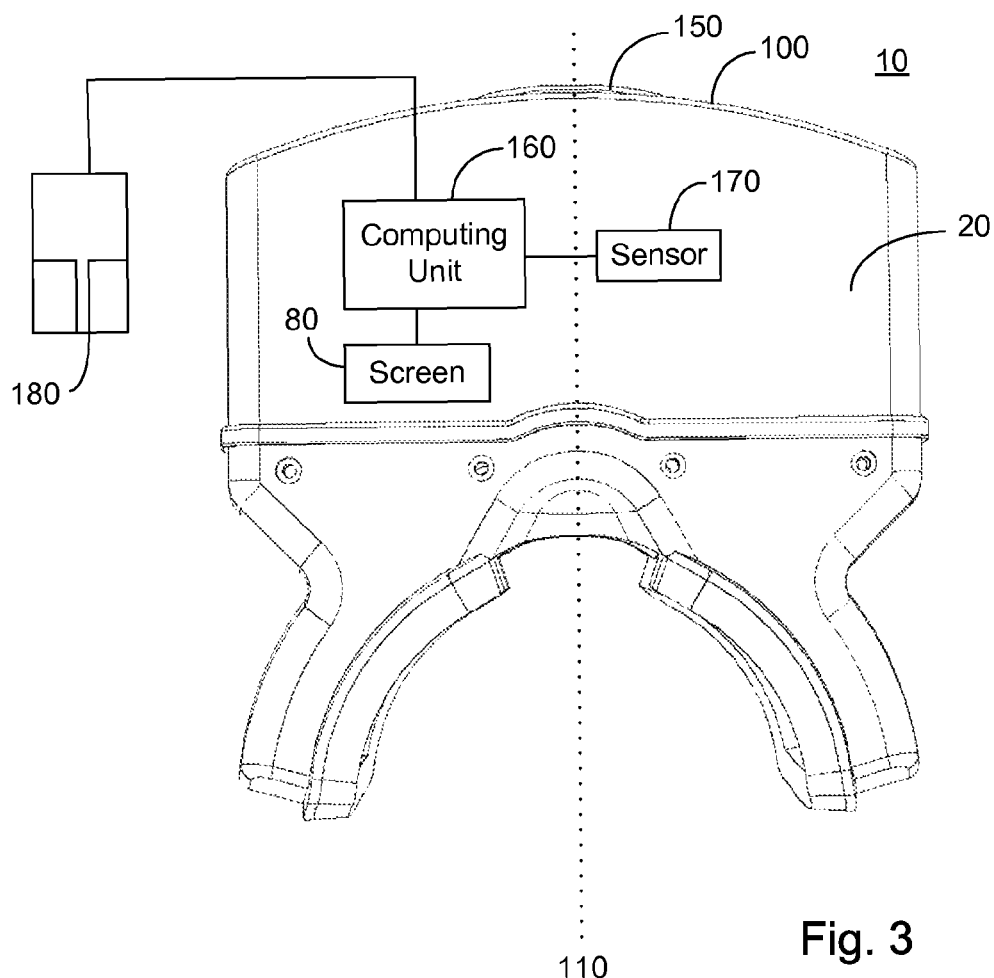
FIG. 3 illustrates a partially cut away top view of an embodiment of an ophthalmic apparatus in accordance with a principle of the current invention.

FIG. 3 illustrates a partially cut away top view of an embodiment of ophthalmic apparatus 10 in accordance with a principle of the current invention. Shown are top wall 20, partially cut away to reveal target object 80, a computing unit 160 and a position sensor 170. Back wall 100 further exhibits an optional stand mounting flange 150. Ophthalmic apparatus 10 further comprises a user input device 180, illustrated without limitation as a pointing device, more particularly illustrated as a mouse. In another embodiment, one of a trackball and a touchpad are provided for user input device 180.

In operation, stand mounting flange 150 is operational to accept a tripod or other stationary footing to support ophthalmic apparatus 10, while allowing for rotation of ophthalmic apparatus 10 about longitudinal axis 110.

Sensor 170, which in one embodiment comprises a gravity sensor, and which will be described further below in relation to FIG. 4, detects whether top wall 20 or bottom wall 40 are face up in relation to a ground surface. In one embodiment, sensor 170 detects if one of top wall 20 and bottom wall 40 are face up. Sensor 170 is in communication with computing unit 160.

Computing unit 160 is operational to display on screen 80 an appropriate image, such as a pattern, or a series of patterns, in accordance with a designed test or therapy, and aligned responsive to sensor 170. In the event that sensor 170 is indicative that top wall 20 is face up, i.e. generally directed towards the users head top, the image or images displayed on screen 80 are thus aligned for viewing by the user's first eye. In the event that sensor 170 is indicative that bottom wall 40 is face up, i.e. generally directed towards the users head top, the image or images displayed on screen 80 are thus aligned for viewing by the user's second eye. In the event that sensor 170 is designed to only indicate if one of top wall 20 and bottom wall 40 are face up, in the absence of a positive indication the reverse is assumed by computing unit 160. In yet another embodiment a manual switch is provided (not shown) to indicate the position of ophthalmic apparatus 10.

Computing unit 160 is further in communication with user input device 180, and in cooperation with a user input via user input device 180 performs an eye test or eye therapy. Thus, for example, in the event that a perimetry test is performed, a user will utilize user input device 180 to indicate test images seen by the eye under test. In one embodiment, in which an eye test is performed, the eye test is one of a perimetry test, a visual acuity test and a contrast sensitivity test. In another embodiment, in which eye therapy is performed, the eye therapy is directed to one of low vision, amblyopia, myopia and strabismus.

Figure 4:
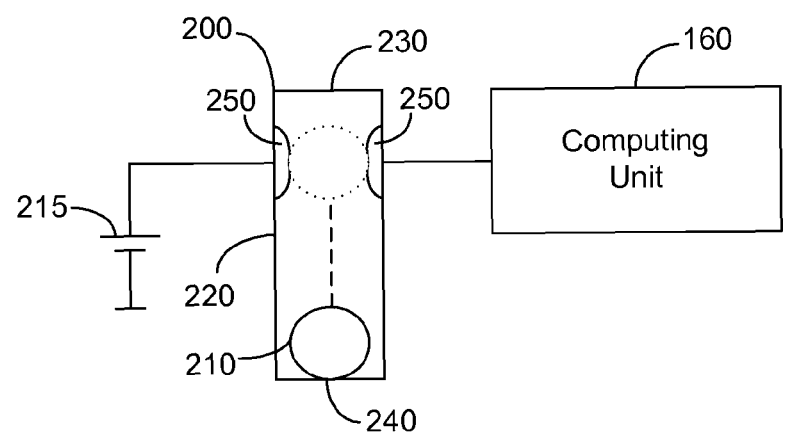
FIG. 4 illustrates an embodiment of a gravity position sensor in accordance with a principle of the current invention.

FIG. 4 illustrates an embodiment of a gravity position sensor 200 in accordance with a principle of the current invention comprising a ball 210 secured within a tube 220 and a signal source 215. Tube 220 exhibits a first end 230 and a second end 240 and is secured within ophthalmic apparatus 10 of FIGS. 1-3. First end 230 is generally facing up coincidentally with top wall 20 facing up, and second end 240 is generally facing up coincidentally with bottom wall 40 facing up. Tube 220 further exhibits a pair of contacts 250 arranged to connect via ball 210 when second end 240 is face up. Signal source 215 is arranged to connect to an input of computing unit 160 via contacts 250 and ball 210 when second end 240 is face up.

In operation, when top wall 20 is face up, first end 230 is face up, and ball 210 is urged by gravity to be removed from contacts 230. Thus the input of computing unit 160 is not in contact with signal source 215. When bottom wall 40 is face up, second end 240 is face up and ball 210 is urged by gravity to be in touch with contacts 250. Computing unit 160 thus receives the output of signal source 215 via contacts 250 and ball 210.

In another embodiment, in place of gravity sensor 200, or in cooperation therewith, a contact sensor is provided on one or more of first indent portion 30 and second indent portion 50. Thus, contact of the user's nose provides positive identification of the position of ophthalmic apparatus 10 in relation to the user's head top in the absence of the user being upright.

In yet another embodiment, in place of gravity sensor 200 or in place of the contact sensor described above, or in cooperation with either or both of them, a light sensor and a luminaire are provided on opposing sections of one or more of first indent portion 30 and second indent portion 50. In one further embodiment the luminaire is constituted of a light emitting diode and the light sensor is constituted of a photodiode. The light sensor and luminaire are placed so that the user's nose will interrupt the light from the luminaire from reaching the light sensor thereby providing automated identification of the position of ophthalmic apparatus 10.

Figure 5:
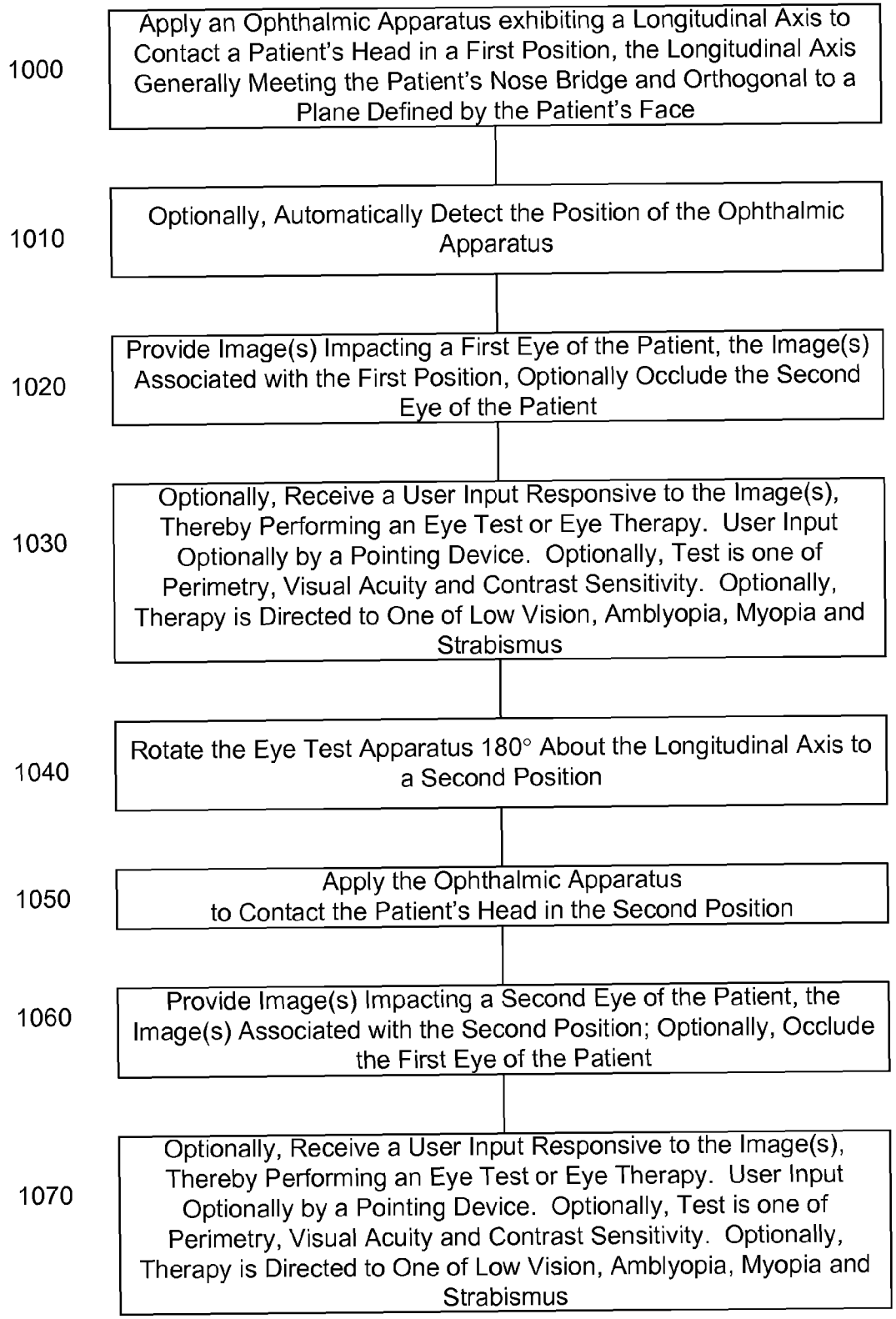
FIG. 5 illustrates a high level flow chart of a method in accordance with a principle of the current invention.

FIG. 5 illustrates a high level flow chart of a method in accordance with a principle of the current invention. In stage 1000 an ophthalmic apparatus, such as eye apparatus 10 of FIG. 1, exhibiting a longitudinal axis, is applied to contact a user's head, with the ophthalmic apparatus in a first position. The longitudinal axis generally meets the user's nose bridge and is orthogonal to a plane defined by the user's face. In stage 1010, optionally, the ophthalmic apparatus automatically detects its own position. In the event that the ophthalmic apparatus is not configured to detect its own position, a user indicates the position to a computing unit associated with the ophthalmic apparatus.

In stage 1020 an image or images are provided, impacting a first eye of the user, the image or images associated with the first position of stage 1000. Optionally, the second eye of the user is occluded. In stage 1030, optionally, a user input responsive to the image, or images, is received, thereby performing one of an eye test and eye therapy. Optionally, user input is provided via a pointing device, such as pointing device 180 of FIG. 3. Optionally, in an embodiment in which an eye test is performed, the eye test is one of perimetry, visual acuity and contrast sensitivity. Optionally, in an embodiment in which eye therapy is performed, in which eye therapy is performed, the eye therapy is directed to one of low vision, amblyopia, myopia and strabismus.

In stage 1040, the ophthalmic apparatus is rotated 180° about the longitudinal axis of stage 1000 to a second position. In stage 1050 the ophthalmic apparatus of stage 1000 in the second position is applied to contact the user's head. In stage 1060 an image or images are provided, impacting a second eye of the user, the image or images associated with the second position of stage 1040. Optionally, the first eye of the user is occluded. In stage 1070, optionally, a user input responsive to the image, or images, is received, thereby performing one of an eye test and eye therapy. Optionally, the user input is provided via a pointing device, such as pointing device 180 of FIG. 3. Optionally, in an embodiment in which an eye test is performed, the eye test is one of perimetry, visual acuity and contrast sensitivity. Optionally, in an embodiment in which eye therapy is performed, in which eye therapy is performed, the eye therapy is directed to one of low vision, amblyopia, myopia and strabismus.

Thus the present embodiments enable a dual position ophthalmic apparatus. The ophthalmic apparatus is changed from a first position to a second position by rotation of the apparatus 180° about a longitudinal axis of the ophthalmic apparatus. Automatic detection of the position is preferably provided and the results of the detection are communicated to a computing unit portion of the ophthalmic apparatus.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

We claim:

1. An ophthalmic apparatus having a first position and a second position, said ophthalmic apparatus comprising:
 a first wall exhibiting a formation at one end for receiving a portion of a user's forehead when the ophthalmic apparatus is in the first position, said first wall generally extending away from said formation of said first wall, said first wall formation further exhibiting a first wall formation indent portion arranged to accommodate the user's nose when the ophthalmic apparatus is in the second position;
 a second wall exhibiting a formation at one end for receiving the portion of the user's forehead when the ophthalmic apparatus is in the second position, said second wall generally opposing said first wall and extending away from said formation of said second wall, said second wall formation further exhibiting a second wall formation indent portion arranged to accommodate the user's nose when the ophthalmic apparatus is in the second position;
 a pair of side walls connecting said first wall to said second wall and forming a light occluding casing in cooperation with said first wall and said second wall; and
 a single target object arranged to be in optical communication with the user's first eye when the ophthalmic apparatus is in said first position and to be in optical communication with the user's second eye when the ophthalmic apparatus is in said second position, said single target object fixed in relationship to said formation of said first wall, said formation of said second wall and said pair of side walls, said fixed relationship to said formations and said side walls unchanged between said first position and said second position,
 wherein said second position represents a 180° rotation of the ophthalmic apparatus from said first position, said rotation being about a longitudinal axis located between said first wall and said second wall, said longitudinal axis generally meeting the bridge of the user's nose and extending in a direction generally orthogonal to a plane defined by the user's face.

2. An ophthalmic apparatus according to claim 1, wherein said first wall formation indent portion and said second wall formation indent portion cooperate to occlude light from the user's eye being tested.

3. An ophthalmic apparatus according to claim 1, wherein said first wall formation indent portion and said second wall formation indent portion cooperate to occlude ambient light from the user's eye being tested.

4. An ophthalmic apparatus according to claim 1, further comprising an occlusion member arranged to occlude the user's second eye when the ophthalmic apparatus is in said first position and to occlude the user's first eye when the ophthalmic apparatus is in said second position.

5. An ophthalmic apparatus according to claim 1, further comprising:
 a sensor operative to detect whether said ophthalmic apparatus is in said first position or in said second position; and
 a computing unit responsive to said sensor,
 wherein said single target object comprises a screen in communication with said computing unit and wherein said computing unit is operative to display at least one image via said screen, said displayed at least one image exhibiting an orientation responsive to said detection of said sensor.

6. An ophthalmic apparatus according to claim 5, wherein said sensor is a gravity sensor.

7. An ophthalmic apparatus according to claim 5, further comprising an input device in communication with said computing unit, said input device operative by said user responsive to said at least one image thereby performing one of an eye test and eye therapy.

8. An ophthalmic apparatus according to claim 7, wherein said input device is a pointing device.

9. An ophthalmic apparatus according to claim 7, wherein said eye test is performed, said eye test at least partially performing one of perimetry, a visual acuity test and a contrast sensitivity test.

10. An ophthalmic apparatus according to claim 7, wherein said eye therapy is performed, said eye therapy directed to one of low vision, amblyopia, myopia and strabismus.

11. A method of performing an eye test, the method comprising:
 providing an ophthalmic apparatus exhibiting:
  a first wall exhibiting a formation at one end for receiving a portion of a user's forehead when the ophthalmic apparatus is in a first position, said first wall generally extending away from said formation of said first wall, said first wall formation further exhibiting a first wall formation indent portion arranged to accommodate the user's nose when the ophthalmic apparatus is in a second position;
  a second wall exhibiting a formation at one end for receiving the portion of the user's forehead when the ophthalmic apparatus is in said second position, said second wall generally opposing said first wall and extending away from said formation of said second wall, said second wall formation further exhibiting a second wall formation indent portion arranged to accommodate the user's nose when the ophthalmic apparatus is in said first position;
  a pair of side walls connecting said first wall to said second wall and forming a light occluding casing in cooperation with said first wall and said second wall; and
  a single target object arranged to be in optical communication with the user's first eye when the ophthalmic apparatus is in said first position and to be in optical communication with the user's second eye when the ophthalmic apparatus is in said second position, said single target object fixed in relationship to said formation of said first wall, said formation of said second wall and said pair of side walls, said fixed relationship to said formations and said side walls unchanged between said first position and said second position,
  said provided ophthalmic apparatus exhibiting a longitudinal axis generally orthogonal to a plane defined by the user's face when receiving the portion of the user's forehead in either said first position or said second position,
 applying said provided ophthalmic apparatus in said first position to receive the portion of the user's forehead in the formation of the first wall, said longitudinal axis generally meeting the bridge of the user's nose;
 providing a first image impacting a first eye of said user, said first image associated with said first position;
 rotating said ophthalmic apparatus 180° about said longitudinal axis to said second position;
 applying said provided ophthalmic apparatus in said second position to receive the portion of the user's forehead in the formation of the second wall; and providing a second image impacting the second eye of said user, said second image associated with said second position.

12. A method according to claim 11, further comprising:
occluding the second eye of said user while providing said first image impacting said first eye of said user; and
occluding the first eye of said user while providing said second image impacting said second eye of said user.

13. A method according to claim 11, further comprising:
automatically detecting the orientation of the ophthalmic apparatus to be one of said first position and said second position; and
providing said first and second images with an orientation responsive to said automatically detected position.

14. A method according to claim 11, further comprising:
receiving a user input responsive to at least one of said provided first image and said provided second image thereby performing one of an eye test and eye therapy.

15. A method according to claim 14, wherein said user input is received via a pointing device.

16. A method according to claim 14, wherein said eye test at least partially performs one of perimetry, a visual acuity test and a contrast sensitivity test.

17. A method according to claim 14, wherein said eye therapy is directed to one of, low vision, amblyopia, myopia and strabismus.

18. An ophthalmic apparatus having a first position and a second position, said ophthalmic apparatus comprising:
a first wall exhibiting a formation at one end for receiving a portion of a user's forehead when the ophthalmic apparatus is in the first position, said first wall generally extending away from said formation of said first wall, said first wall formation further exhibiting a first wall formation indent portion arranged to accommodate the user's nose when the ophthalmic apparatus is in the second position;
a second wall exhibiting a formation at one end for receiving the portion of the user's forehead when the ophthalmic apparatus is in the second position, said second wall generally opposing said first wall and extending away from said formation of said second wall, said second wall formation further exhibiting a second wall formation indent portion arranged to accommodate the user's nose when the ophthalmic apparatus is in the second position;
a pair of side walls connecting said first wall to said second wall and forming a light occluding casing in cooperation with said first wall and said second wall;
a means for displaying a single target object to be in optical communication with the user's first eye when the ophthalmic apparatus is in said first position and to be in optical communication with the user's second eye when the ophthalmic apparatus is in said second position, said means for displaying a single target object fixed in relationship to said formation of said first wall, said formation of said second wall and said pair of side walls, said fixed relationship to said formations and said side walls unchanged between said first position and said second position; and
a means for automatic detection as to whether the ophthalmic apparatus is in the first position or in the second position, said means for displaying responsive to said means for automatic detection,
wherein said second position represents a 180° rotation of the ophthalmic apparatus from said first position, said rotation being about a longitudinal axis located between said first wall and said second wall, said longitudinal axis generally meeting the bridge of the user's nose and extending in a direction generally orthogonal to a plane defined by the user's face.

* * * * *